United States Patent
Gu et al.

(10) Patent No.: US 11,395,844 B2
(45) Date of Patent: Jul. 26, 2022

(54) PUERARIA FLOWER EXTRACT RICH IN ISOFLAVONES AND A METHOD AND APPLICATION OF THE SAME

(71) Applicants: Sujing Gu, Luohe (CN); Linzheng Li, Luohe (CN); Ziheng Jin, Luohe (CN); Yanjun Wen, Luohe (CN)

(72) Inventors: Sujing Gu, Luohe (CN); Linzheng Li, Luohe (CN); Ziheng Jin, Luohe (CN); Yanjun Wen, Luohe (CN)

(73) Assignee: HENAN ZHONGDA HENGYUAN BIOTECHNOLOGY STOCK CO., LTD., Henan (CN)

( * ) Notice: Subject to any disclaimer, the term of this patent is extended or adjusted under 35 U.S.C. 154(b) by 0 days.

(21) Appl. No.: 17/327,708

(22) Filed: May 22, 2021

(65) Prior Publication Data
US 2021/0393725 A1 Dec. 23, 2021

(30) Foreign Application Priority Data

Jun. 22, 2020 (CN) .......................... 202010571300.0

(51) Int. Cl.
*A61K 36/488* (2006.01)
(52) U.S. Cl.
CPC ........ *A61K 36/488* (2013.01); *A61K 2236/15* (2013.01); *A61K 2236/333* (2013.01); *A61K 2236/53* (2013.01)

(58) Field of Classification Search
None
See application file for complete search history.

(56) References Cited

U.S. PATENT DOCUMENTS 8,333,999 B2 * 12/2012 Chen ...................... C12M 45/02
424/773

OTHER PUBLICATIONS

CN104844584A (English translation from https://worldwide.espacenet.com/) (Year: 2015).*

* cited by examiner

*Primary Examiner* — Michael Barker

(57) ABSTRACT

A method of preparing a *Pueraria* flower extract rich in isoflavones includes: grinding dry *Pueraria* flowers to obtain a *Pueraria* flower powder; adding a first 20-50% ethanol solution to form a mixture, stirring and heating the mixture at 20-80° C. for 1-4 hours, removing the first solution, adding a second 20-50% ethanol solution, stirring and heating the mixture, removing the second solution, and combining the first solution and the second solution to obtain an extract solution; filtering the extract solution to remove solids; concentrating the extract solution under vacuum to obtain a crude extract containing 10-40% solid components; adding anhydrous ethanol solution to reach an ethanol concentration of the crude extract of 75-95%, storing the crude extract at 20-30° C. for 1-4 hours; centrifuging the crude extract at a speed of 2,000-5,000 r/min to obtain a supernatant; and concentrating and spray drying to obtain the *Pueraria* flower extract without any purification steps.

8 Claims, No Drawings

PUERARIA FLOWER EXTRACT RICH IN ISOFLAVONES AND A METHOD AND APPLICATION OF THE SAME

This application claims priority to Chinese Patent Application No. 202010571300.0, filed on Jun. 22, 2020, which is incorporated by reference for all purposes as if fully set forth herein.

TECHNICAL FIELD

The invention relates to medicine and food, and in particular, to a *Pueraria* flower extract rich in isoflavones and a method and application of the same.

BACKGROUND TECHNIQUE

*Pueraria* flower is the dried flower of plant *Puerarialobata* (Willd.) *Ohwi*. It is included in the Medicine Standards of the Ministry of Health of the People's Republic of China, Chinese Medicinal Materials. It is non-toxic, has a sweet and cool medicinal nature, and is used to relieve hangover. It can be used for symptoms, such as excessive drinking, headache, dizziness, polydipsia, vomiting and heartburn. In addition, modern studies have found that *Pueraria* flower also has the effects of lowering blood sugar, lowering blood fat, antioxidant, anti-allergic, improving memory, lowering body fat and losing weight. *Pueraria* flower contains flavonoids, saponins, and volatile oil compounds. The most studied active ingredients are isoflavones, such as iris, *Pueraria lobata*, and Nepal iris.

The extraction process of *Pueraria* flower mainly uses water extraction and organic solvent extraction to obtain extracts with or without refining, but the extracts obtained by these methods have low isoflavone content, or the cumbersome process has low yield. The extract is not soluble in water, and is difficult to meet the requirements of the beverage and food industry. CN 101239092 A discloses *Pueraria* flower isoflavone extract, its extraction method, pharmaceutical composition and its application in pharmacy. Although the solubility is improved, the method requires extraction with an organic solvent after alumina treatment. The operation steps are complicated, and the extraction rate is low and operation cost is high. CN 101129447 A also discloses a method and application for extracting total isoflavones from *Pueraria* flowers. The method includes adding 10-60% ethanol to dilute the ethanol extraction extract to prepare the high-content isoflavone extract by using a macroporous adsorption resin. This process requires high energy consumption and has high cost.

SUMMARY OF THE INVENTION

In order to overcome the deficiencies described in the background art, the purpose of the present invention is to solve the application problem of the solubility of *Pueraria* flower extract in food and the problem of quality improvement, and to provide a good water-soluble extract of *Pueraria* flower rich in isoflavones and an easy to operate, low-cost preparation method.

In one embodiment, a method of preparing a *Pueraria* flower extract rich in isoflavones includes the following steps:

(1) grinding dry *Pueraria* flowers to obtain a *Pueraria* flower powder;

(2) adding a first 20-50% ethanol solution to the *Pueraria* flower powder to form a mixture, stirring and heating the mixture at 20-80° C. for 1-4 hours, removing the first 20-50% ethanol solution from the mixture, adding a second 20-50% ethanol solution to the mixture, stirring and heating the mixture at 20-80° C. for 1-4 hours, removing the second 20-50% ethanol solution from the mixture, and combining the first 20-50% ethanol solution and the second 20-50% ethanol solution to obtain an extract solution;

(3) filtering the extract solution to remove solids;

(4) concentrating the extract solution under vacuum to obtain a crude extract, the crude extract containing 10-40% solid components;

(5) adding anhydrous ethanol solution to the crude extract to reach an ethanol concentration of the crude extract of 75-95%, storing the crude extract at 20-30° C. for 1-4 hours;

(6) centrifuging the crude extract at a speed of 2,000-5,000 r/min to obtain a supernatant; and (7) concentrating the supernatant under vacuum, and spray drying to obtain the *Pueraria* flower extract without any purification steps.

In another embodiment, in step (2), a weight ratio of the *Pueraria* flower powder:the combination of the first 20-50% ethanol solution and the second 20-50% ethanol solution is 1:5-10.

In another embodiment, in step (2), the weight ratio of the *Pueraria* flower powder:the combination of the first 20-50% ethanol solution and the second 20-50% ethanol solution is 1:6.

In another embodiment, the step (2) includes: adding a first 30-40% ethanol solution to the *Pueraria* flower powder to form a mixture, stirring and heating the mixture at 60-80° C. for 1-2 hours, removing the first 30-40% ethanol solution from the mixture, adding a second 30-40% ethanol solution to the mixture, stirring and heating the mixture at 60-80° C. for 1-2 hours, removing the second 30-40% ethanol solution from the mixture, and combining the first 30-40% ethanol solution and the second 30-40% ethanol solution to obtain an extract solution.

In another embodiment, the step (2) includes: adding a first 40% ethanol solution to the *Pueraria* flower powder to form a mixture, stirring and heating the mixture at 60° C. for 1 hour, removing the first 40% ethanol solution from the mixture, adding a second 40% ethanol solution to the mixture, stirring and heating the mixture at 60° C. for 1 hour, removing the second 40% ethanol solution from the mixture, and combining the first 40% ethanol solution and the second 40% ethanol solution to obtain an extract solution.

In another embodiment, in the step (4), the crude extract contains 25% solid components.

In another embodiment, the step (5) includes: adding anhydrous ethanol solution to the crude extract to reach an ethanol concentration of the crude extract of 80%, storing the crude extract at 20° C. for 1-4 hours.

In another embodiment, the step (6) includes: centrifuging the crude extract at a speed of 3000 r/min to obtain a supernatant.

The invention provides an application of the *Pueraria* flower extract extract rich in isoflavones in foods, health products and medicines, especially in beverages and oral liquids.

Compared with the prior art, the *Pueraria* flower extract obtained by the present invention has excellent solubility in water, high content of *Pueraria* flower isoflavones and high yield, and can be used in food, beverages and oral liquids. The process operation is simple and feasible, and is suitable for industrial production.

DETAILED DESCRIPTION

Example 1

1 kg of dried *Pueraria* flower raw material was grinded to obtain a powder, and powder was passed through 40 mesh sieves. 3 kg of 40% ethanol was added, and the mixture was stirred and heated at 60° C. for 1 hour for extraction. The ethanol extraction solution was collected. Additional 3 kg of 40% ethanol was added, and the mixture was stirred and heated at 60° C. for 1 hour for extract. The ethanol extraction solution was collected and combined with the ethanol extraction solution from the first extraction. The combined ethanol extraction solution was filtered to remove solids and concentrated under reduced pressure to obtain a crude extract that includes 25% solid components. Anhydrous ethanol was added to the crude extract to an ethanol concentration of 80%. The crude extract solution was placed at room temperature for 2 hours, and a precipitate was formed. The crude extract solution was centrifuged at 3000 r/min for 10 minutes, and the supernatant was collected and concentrated under reduced pressure to remove ethanol to obtain an extract. The extract was then spray-dried to obtain 187 g of *Pueraria* flower extract. The yield of isoflavones was 92.6%, and the isoflavones content was 32.2%. A 1% aqueous solution of the *Pueraria* flower extract was clear and bright, with a turbidity of 12.4 NTU.

Example 2

1 kg of dried *Pueraria* flower raw material was grinded to obtain a powder, and powder was passed through 40 mesh sieves. 3 kg of 40% ethanol was added, and the mixture was stirred and heated at 60° C. for 1 hour for extraction. The ethanol extraction solution was collected. Additional 3 kg of 40% ethanol was added, and the mixture was stirred and heated at 60° C. for 1 hour for extract. The ethanol extraction solution was collected and combined with the ethanol extraction solution from the first extraction. The combined ethanol extraction solution was filtered to remove solids and concentrated under reduced pressure to obtain a crude extract that includes 40% solid components. Anhydrous ethanol was added to the crude extract to an ethanol concentration of 80%. The crude extract solution was placed at room temperature for 2 hours, and a precipitate was formed. The crude extract solution was centrifuged at 3000 r/min for 10 minutes, and the supernatant was collected and concentrated under reduced pressure to remove ethanol to obtain an extract. The extract was then spray-dried to obtain 155.6 g of *Pueraria* flower extract. The yield of isoflavones was 27.1%, and the isoflavones content was 11.3%. A 1% aqueous solution of the *Pueraria* flower extract was clear and bright, with a turbidity of 19.7 NTU.

Example 3

1 kg of dried *Pueraria* flower raw material was grinded to obtain a powder, and powder was passed through 40 mesh sieves. 3 kg of 50% ethanol was added, and the mixture was stirred and heated at 60° C. for 1 hour for extraction. The ethanol extraction solution was collected. Additional 3 kg of 50% ethanol was added, and the mixture was stirred and heated at 60° C. for 1 hour for extract. The ethanol extraction solution was collected and combined with the ethanol extraction solution from the first extraction. The combined ethanol extraction solution was filtered to remove solids and concentrated under reduced pressure to obtain a crude extract that includes 10% solid components. Anhydrous ethanol was added to the crude extract to an ethanol concentration of 80%. The crude extract solution was placed at room temperature for 2 hours, and a precipitate was formed. The crude extract solution was centrifuged at 3000 r/min for 10 minutes, and the supernatant was collected and concentrated under reduced pressure to remove ethanol to obtain an extract. The extract was then spray-dried to obtain 231.2 g of *Pueraria* flower extract. The yield of isoflavones was 91.4%, and the isoflavones content was 25.7%. A 1% aqueous solution of the *Pueraria* flower extract was clear and bright, with a turbidity of 37.4 NTU.

Finally, the above-mentioned embodiments are merely examples for clearly illustrating the present invention, rather than limiting the implementation manners. For those of ordinary skill in the art, other changes or changes in different forms can be made on the basis of the above description. There is no need to give an exhaustive list of all implementation methods. The obvious changes or changes derived from this are still within the protection scope of the present invention.

The invention claimed is:

1. A method of preparing a *Pueraria* flower extract rich in isoflavones consisting of the following steps:
   (1) grinding dry *Pueraria* flowers to obtain a *Pueraria* flower powder;
   (2) adding a first 20-50% ethanol solution to the *Pueraria* flower powder to form a mixture, stirring and heating the mixture at 20-80° C. for 1-4 hours, removing the first 20-50% ethanol solution from the mixture, adding a second 20-50% ethanol solution to the mixture, stirring and heating the mixture at 20-80° C. for 1-4 hours, removing the second 20-50% ethanol solution from the mixture, and combining the first 20-50% ethanol solution and the second 20-50% ethanol solution to obtain an extract solution;
   (3) filtering the extract solution to remove solids;
   (4) concentrating the extract solution under vacuum to obtain a crude extract, the crude extract containing 10-40% solid components;
   (5) adding anhydrous ethanol solution to the crude extract to reach an ethanol concentration of the crude extract of 75-95%, storing the crude extract at 20-30° C. for 1-4 hours;
   (6) centrifuging the crude extract at a speed of 2,000-5,000 r/min to obtain a supernatant; and
   (7) concentrating the supernatant under vacuum, and spray drying to obtain the *Pueraria* flower extract without any purification steps.

2. The method of claim 1, wherein in step (2), a weight ratio of the *Pueraria* flower powder:a combination of the first 20-50% ethanol solution and the second 20-50% ethanol solution is 1:5-10.

3. The method of claim 2, wherein in step (2), the weight ratio of the *Pueraria* flower powder:the combination of the first 20-50% ethanol solution and the second 20-50% ethanol solution is 1:6.

4. The method of claim 1, wherein the step (2) consists of: adding a first 30-40% ethanol solution to the *Pueraria* flower powder to form a mixture, stirring and heating the mixture at 60-80° C. for 1-2 hours, removing the first 30-40% ethanol solution from the mixture, adding a second 30-40% ethanol solution to the mixture, stirring and heating the mixture at 60-80° C. for 1-2 hours, removing the second 30-40% ethanol solution from the mixture, and combining the first 30-40% ethanol solution and the second 30-40% ethanol solution to obtain an extract solution.

5. The method of claim 4, wherein the step (2) consists of: adding a first 40% ethanol solution to the *Pueraria* flower powder to form a mixture, stirring and heating the mixture at 60° C. for 1 hour, removing the first 40% ethanol solution from the mixture, adding a second 40% ethanol solution to the mixture, stirring and heating the mixture at 60° C. for 1 hour, removing the second 40% ethanol solution from the mixture, and combining the first 40% ethanol solution and the second 40% ethanol solution to obtain an extract solution.

6. The method of claim 1, wherein in the step (4), the crude extract contains 25% solid components.

7. The method of claim 1, wherein the step (5) consists of: adding anhydrous ethanol solution to the crude extract to reach an ethanol concentration of the crude extract of 80%, storing the crude extract at 20° C. for 1-4 hours.

8. The method of claim 1, wherein the step (6) consists of: centrifuging the crude extract at a speed of 3000 r/min to obtain a supernatant.

* * * * *